United States Patent [19]

Wysor et al.

[11] Patent Number: 5,891,915

[45] Date of Patent: Apr. 6, 1999

[54] METHOD FOR ENHANCING FEMALE SEXUAL RESPONSE AND AN OINTMENT THEREFOR

[76] Inventors: Michael S. Wysor; Wanda D. Wysor, both of 1171 First St., Gray, Tenn. 37615

[21] Appl. No.: 71,436

[22] Filed: May 1, 1998

[51] Int. Cl.$^6$ .................................................. A61K 31/19

[52] U.S. Cl. ............................................................ 514/573

[58] Field of Search ............................................... 514/573

[56] References Cited

U.S. PATENT DOCUMENTS 4,352,790  10/1982  Johansson et al. ........................ 424/78
5,773,020   6/1998  Place et al. .............................. 424/426

*Primary Examiner*—Raymond Henley, III
*Attorney, Agent, or Firm*—Michael Ebert

[57] ABSTRACT

A method for enhancing female sexual response in which topically administered to the clitoris of the female subject and the surrounding tissue is a pharmaceutically-acceptable ointment containing a prostaglandin of the "E" series.

5 Claims, No Drawings

METHOD FOR ENHANCING FEMALE SEXUAL RESPONSE AND AN OINTMENT THEREFOR

BACKGROUND OF INVENTION

1. Field of Invention

This invention relates generally to compositions for treating impotence, and more particularly to a method for enhancing female sexuality by topically administering a composition of this type in an ointment form which is applied to the clitoris and the surrounding tissue of the female subject and is absorbed thereby.

2. Status of Prior Art

The term impotence, as applied to sexuality, usually refers to the inability of a male to attain or sustain penile erection. But it is also applicable to aberrations of sexual function in a female, either because of lack of sexual desire or failure to attain orgasm. Hence female frigidity is effectively, female impotence.

In the treatment of male impotence it is known to use for this purpose prostaglandins of the E series. One commercially-available form of this composition is identified as Alprostadil, a naturally occurring prostaglandin E-1. This composition is disclosed in "Mechanisms of Action" in Alprostadil Clinical Pharmacology on "physicians on Line" (http://www.gsm.com). Also of prior art interest is the Scott U.S. Pat. No. 5,708,031 (1998) which discloses the use of prostaglandin E-2 in the treatment of impotence.

Alprostadil is used to treat impotence in adult males and to maintain the potency of the ductus arteriosus in neonates. Two dosage forms are marketed for treating impotence: an injection form (Caverjet or Edex) that is directly injected into the corpus cavernosa of the penis, and a trans-urethral product, (Muse), which uses a medicated pellet administered into the urethra.

When treating male impotence, Alprostadil relaxes the smooth muscle of the corpus cavernosum. However, the exact mechanism of this action is unknown. The drug may work by increasing the intracellular concentrations of cyclic AMP. Alprostadil interacts with specific membrane bound receptors, thus stimulating adenylate cyclase and elevating intracellular cyclic AMP, leading to the activation of protein kinase with resultant smooth muscle relaxation. Dilation of the cavernosal arteries is accompanied by increased arterial inflow velocity and increased venous outflow resistance. Lacunar spaces expand and blood becomes entrapped secondary to compression of the venule against the tunica albuginea. This process is referred to as the corporal veno-occlusive mechanism.

Alprostadil has heretofore been limited to treating male sexual dysfunction. It has not been used to treat female sexual problems, such as frigidity, nor to enhance female sexual response.

Lack of sexual desire or failure to attain organism is much more frequent in the female than in the male. It occurs in a significant percentage of neurotic women, as well as others who exhibit no signs of psychic disorder. (see: Principles of Neurology—Adams and Victor—Third Edition—McGraw Hill Book Company). Yet heretofore no effective pharmaceutical preparations for treating women who have difficulty in responding sexually have been available.

SUMMARY OF INVENTION

In view of the foregoing, the main object of this invention is to provide a method for enhancing female sexual response and a composition to be administered in carrying out this method.

More particularly, an object of the invention is to provide a method of the above type which topically administers to the clitoris of the female being treated and the surrounding tissue a pharmaceutically-acceptable composition containing a prostaglandin of the "E" series.

DESCRIPTION OF INVENTION

We have discovered a method of significantly enhancing female sexual response by treating the clitoris and the immediate surrounding tissues of a female subject with a pharmaceutically acceptable formulation containing a prostaglandin of the "E" series, particularly prostaglandin E-1 (Alprostadil). The dosage is that which elicits a maximal sexual response in the subject, yet has minimal toxicity.

The main benefits of this treatment are:

A. Anorgasmic women (frigidity or impotence)

B. Intermittently anorgasmic women

C. Orgasmic women seeking greater sexual response

This is accomplished by Alprostadil therapy of the clitoris and surrounding tissue by one or more of the following in various permutations and combinations:

1. Decreasing foreplay (the period necessary to prepare women for intercourse).

2. Decreasing the latency period (i.e. the period between orgasms).

3. Decreasing the intercourse time required for orgasm.

4. Multiplying the number of orgasms.

Alprostadil, when applied topically to the clitoris and surrounding tissue of a female subject in a pharmaceutically—acceptable formulation in a dosage range sufficient to elicit one or more of the above-mentioned sexual responses (1–4) is then highly effective for this purpose.

An ointment or salve is the preferred form for delivering the composition. In practice, the ointment may be packaged in a squeeze tube or it may be impregnated in a gauze or foam plastic sponge applicator.

We have found that the topical administration of 21.25 micrograms per milliliter of Alprostadil in a pharmaceutically-acceptable ointment base to the clitoris and the immediate surrounding tissues is sufficient to produce an absorption of Alprostadil into this region to effect enhanced sexual response in three to four minutes (on the average), thereby decreasing the foreplay period for intercourse and the latency period as well as the sexual intercourse time required for orgasm. The treatment also acts to multiply the number of orgasms. But the dosage is not critical, for even a relatively small amount of Alprostadil absorbed in the region of the clitoris will to some degree enhance sexual response.

By pharmaceutically-acceptable formulation is meant a formulation that is free of toxicity and satisfies FDA requirements.

While there has been disclosed a preferred formulation in accordance with the invention and a method of administering this composition so as to enhance female sexual response, it will be appreciated that many changes may be made therein without departing from the spirit of the invention.

We claim:

1. A method of enhancing sexuality in a female having a clitoris comprising topically administering to the clitoris a composition that includes a prostaglandin of the "E" series.

2. A method as set forth in claim 1, in which the prostaglandin is E-1.

3. A method as set forth in claim 1, in which the composition is also applied to tissue surrounding the clitoris whereby it is absorbed thereby.

4. A method as set forth in claim 1, in which the composition includes an ointment base whereby the composition is retained on the clitoris and the prostaglandin is absorbed thereby.

5. A method as set forth in claim 1, in which the composition is in a dosage sufficient to elicit a maximum sexual response with minimal toxicity.

* * * * *